(12) United States Patent
Cuberes Altisen et al.

(10) Patent No.: US 7,232,812 B2
(45) Date of Patent: Jun. 19, 2007

(54) SUBSTITUTED AZETIDINE COMPOUNDS, THEIR PREPARATION AND USE AS MEDICAMENTS

(75) Inventors: Rosa Cuberes Altisen, Barcelona (ES); Jordi Frigola Constansa, Barcelona (ES); Ines Alvarez Mathieu, Barcelona (ES)

(73) Assignee: Laboratorios de Dr. Esteve S.A., Barcelona (ES)

( * ) Notice: Subject to any disclaimer, the term of this patent is extended or adjusted under 35 U.S.C. 154(b) by 71 days.

(21) Appl. No.: 10/804,505

(22) Filed: Mar. 19, 2004

(65) Prior Publication Data

US 2005/0182041 A1 Aug. 18, 2005

(30) Foreign Application Priority Data

Feb. 16, 2004 (ES) .............................. 200400363

(51) Int. Cl.
*A61K 31/397* (2006.01)
*C07D 205/04* (2006.01)

(52) U.S. Cl. .......................... 514/210.17; 514/210.18; 548/952; 548/953

(58) Field of Classification Search .................... None
See application file for complete search history.

(56) References Cited

U.S. PATENT DOCUMENTS

| 5,073,646 A | 12/1991 | Pinol et al. | 548/953 |
| 5,925,672 A * | 7/1999 | Piomelli et al. | 514/460 |
| 6,004,948 A | 12/1999 | Blaschke et al. | 514/155 |
| 6,472,416 B1 | 10/2002 | Kolasa et al. | 514/403 |

FOREIGN PATENT DOCUMENTS

| DE | 299 21 689 U1 | 5/2001 |
| EP | 0 406 112 A1 | 6/1990 |
| EP | 1 364 949 A1 | 11/2003 |
| WO | WO 2004/011421 A1 | 2/2004 |

OTHER PUBLICATIONS

Otani et al., "An Evaluation of Amide Group Planarity in 7-Azabicyclo[2.2.1]heptane Amides. Low Amide Bond Rotation Barrier in Solution," J. Am. Chem. Soc., vol. 125(49) pp. 15191-15199 (2003).*
Wallace et al., "Emerging roles for cyclooxygenase-2 in gastrointestinal mucosal defense," Br. J. Pharmacol., 145, 275-282, 275 (2005).*
Wallace, "COX-2: A Pivitol Enzyme in Mucosal Protection and Resolution of Inflammation," The Scientific World J., 6, 577-588, 578 (2006).*
"Health Aspects of Cannabis", Leo E. Hollister, Pharmacological Reviews, 38, 1986, 1-20.
"Chemistry and pharmacology of cannabis", Renu Seth et al., Prog-Drug-Res., 1991, vol. 36, p. 71-115.
"Potential Role of Cannabinoids for Therapy of Neurological Disorders", Consroe and Sandyk, Neurobiology and Neurophysiology, 1992, 459-524.
"Novel Syntheses of 1,3,3-Trinitroazetidine", Alan R. Katritzky, et al., J. Heterocyclic Chem. 31, 271-275 (1994).
"Acylative Dealkylation of *N-Tert*-Butyl-3-substituted Azetidines: Facile Access to [1.1.0] Azabicyclobutane, 3-Hydroxyazetidinium Hydrochloride, and 3-Azetidinones", Paritosh R. Dave, J. Org. Chem. 1996, 61, 5453-5455.
"Synthesis of Novel Four-Membered Ring Amino Acids as Modulators of the N-Methyl-D-Aspartate (NMDA) Receptor Complex", Alan P. Kozikowski, et al., Synlett. 1991, (11), 783-784.
"Synthesis of 1,3,3-Trinitroazetidine", Theodore Axenron, et al., Tetrahedron Letters, vol. 34, No. 42, pp. 6677-6680, 1993.
"The selective formation of unsaturated alcohols by hydrogenation of α,β-unsaturated aldehydes in supercritical carbon dioxide using unpromoted $Pt/Al_2O_3$ catalyst", Bhalchandra M. Bhanage, et al., Catalysis Letters 62 (1999) 175-177.
"Studies of β-Methyl-1-and 3-Phenyl Allyl Chlorides", M.Y. Shandala, et al., Tetrahedron vol. 40 No. 7, pp. 1195 to 1198, 1984.
"Selective Reduction of Carbonyl Compounds by Polymethylhydrosiloxane in the Presence of Metal Hydride Catalysts", Hubert Mimoun et al., J. Org. Chem. 1999, 64, 2582-2589.
"Catalytic Asymmetric Cyclopropanation of Allylic Alcohols with Titanium-TADDOLate: Scope of the Cyclopropanation Reaction", Andre B. Charette, et al., J. Am. Chem. Soc. 2001, 123, 12168-12175.
"Thionyl Chloride-Benzotriazole in Methylene Chloride: A Convenient Solution for Conversion of Alcohols and Carboxylic Acids Expeditiously in Alkyl Chlorides and Acid Chlorides by Simple Titration", Sachin S. Chaudhari, et al., Synlett 1999, No. 11, 1763-1765.
"Activation de la liaison silicium-halogene par les halogenures de bismuth (III). Halogenation des alcohols: perspectives et mecanisme [1]", Mireille Labrouillere, et al., Bull Soc Chim Fr (1995) 132, 522-530.
"Synthese of Two Cytotoxic Sinapyl Alcohol Derivatives and Isolation of Four New Related Compounds from *Ligularia nelumbifolia*" Yu Zhao, et al., J. Nat. Prod. 2002, 65, 902-908.
"Towards an Understanding of Cram/*anti*-Cram selectivity on Addition of Crotylboronates to α-Methylbutyraldehyde", Reinhard W. Hoffman, Chem. Ber. 123 (1990) 2387-2394.
"Stereospecific Synthesis of 2,3,6-Trisubstituted Piperidines: An Efficient Total Synthesis of (±)-Pumiliotoxin C", Norman A. LeBel, et al., J. Am. Chem. Soc. 1989, 111, 3363-3368.
"Triphenylphosphine/Dichloroselenurane: A New Reagent for a Selective Conversion of Alcohols into Alkyl Chlorides", Jozef Drabowicz, et al., J. Org. Chem. 1998, 63, 9565-9568.
"Formation of indole nucleus via intramolecular cyclization of aminophenylpropenyltriphenylphosphonium salts with one-carbon degradation", Shin'ichi Taira et al., Tetrahedron Letters 43 (2002) 8893-8896.

(Continued)

*Primary Examiner*—Joseph K. McKane
*Assistant Examiner*—Andrew B. Freistein
(74) *Attorney, Agent, or Firm*—Perman & Green, LLP

(57) ABSTRACT

The present invention relates to substituted Azetidine compounds of general formula (I), methods for their preparation, medicaments comprising these compounds as well as their use for the preparation of a medicament for the treatment of humans and animals.

26 Claims, No Drawings

OTHER PUBLICATIONS

"Benzophenone Derivatives and Related Compounds as Potent Histamine $H_3$-Receptor Antagonists and Potential PET/SPECT Ligands", Astrid Sasse, et al., Arch. Pharm. Pharm. Med. Chem. 2001, 334(2), 45-52.

"Stereoselective Syntheses of Spicy Components in Peppers", Akihiro Ohta, et al., Heterocycles, vol. 32, No. 5, 1991, 965-973.

"Negative Inotropic and Calcium Antagonistic Activity of Alkyl and Arylalkyl Phosphonates", Cristina Bellucci, et al., IL FARMACO, 44 (12), 1167-1191; 1989.

"Synthesis of 6-(3-Aryl-2-propenyl)-2, 3-dihydro-5-hydroxybenzofuran Derivatives by Cross Coupling Reactions", Ramon J. Alabaster, et al., Synthesis, 8, 598-603, 1989.

"Antioxidant-Based Inhibitors of Leukotriene Biosynthesis. The Discovery of 6-[1-[2-(Hydroxymethyl)phenyl]-1-propen-3-yl]-2,3-dihydro-5-benzofuranol, a Potent Topical Antiinflamatory Agent", Milton L. Hammond, et al., J. Med. Chem. 1990, 33, 908-918.

"Configurational Analysis of 1-Alkyl-2-Methylazetidin-3-ols", Robert H. Higgins, et al., J. Heterocyclic Chem., 1971, 8, 1059-1062.

"New Synthesis of 2-Azetines and 1-Azabutadienes and the Use of the Latter in Diels-Alder Reactions: Total Synthesis of (±)-δ-Coniceine", Michael E. Jung, et al., J.O.C., 1991, 6729-30.

"Cyclization of 1-Alkylamino-3-halo-2-alkanols to 1-Alkyl-3-azetidinols", V.R. Gaertner, J. Org. Chem., 1967, 32, 2972-2976.

"Solid-Phase Synthesis of Oximes", Hajipour, A.R., et al., Synthetic Communications, 29(10), 1697-1701 (1999).

"A Short, Efficient Synthesis of Substituted Uracil: An Indane Carbocyclic Nucleoside", Franco Fernandez, et al., Synthesis 2001, No. 2, 239-242.

"Benzhydryl and Fluorenyl Lactamimides with Hypoglycemic, Diuretic, Blood Platelet Aggregation Inhibitory, and Antiinflamatory Activities", J. Martin Grisar, et al., Journey of Medicinal Chemistry, 1973, vol. 16, No. 8, 885-893.

"Synthesis of Substituted Benzhydrylamines", Yves Dejaegher, et al., Synlett 2002, No. 1, Dec. 28, 2001, Article Identifier: 1437-2096, E; 2002, 0, 01, 0113, 0115, ftx, en; G16101ST.pdf., pp. 113-115.

"7-Azetidinylquinolones as Antibacterial Agents. Synthesis and Structure-Activity Relationships", Jordi Frigola et al., J. Med. Chem. 1993, 36, 801-810.

7-Azetidinylquinolones as Antibacterial Agents. $2._I$ Synthesis and Biological Activity of 7-(2,3-Disubstituted-1-azetidinyl)-4-oxoquinoline- and -1,8-naphthyridine-3-carboxylic Acids. Properties and Structure-Activity Relationships of Quinolones with an Azetidine Moiety, Jordi Frigola, et al., J. Med. Chem. 1994, 37, 4195-4210.

"7-Azetidinylquinolones as Antibacterial Agents. 3. Synthesis, Properties and Structure-Activity Relationships of the Stereoisomers Containing a 7-(3-Amino-2-methyl-1-azetidiny) Moiety", Jordi Frigola, et al., J. Med. Chem. 1995, 38, 1203-1215.

"The First Practical Method for Asymmetric Epoxidation", Ramanuj Goswami, J. Am. Chem. Soc. 1980, 102, 5974-5976.

"Progress toward the Total Synthesis of Bafilomycin $A_1$: Stereoselective Synthesis of the C15-C25 Subunit by Additions of Nonacemic Allenylzinc Reagents to Aldehydes", James A. Marshall, et al., Organic Letters, 2000, vol. 2, No. 18 2897-2900.

"Amberlyst-15($H^+$)-$NaBH_4$-LiCl: An Effective Reductor for Oximes and Hydrazones", Bipul Baruah et al., Synlett 1999, No. 4, 409-410.

"The Synthesis of Azetidine-3-carboxylic Acid", Arthur G. Anderson, Jr., J. Org. Chem., vol. 57, No. 24, 1972, 3953-3955.

"The Azetidines, Recent Synthetic Developments", Norman H. Cromwell, et al., Chem. Rev., 1979, 79, 331-358.

"Synthese de l' amino-3 azetidine" Dino Nisato, et al., J. Heterocyclic Chem. 22, 961-963 (1985).

"A Short Enantioselective Synthesis of N-Boc-α-Amino Acids from Epoxy Alchohols", Marta Poch, et al., Tetrahedron Letters, vol. 34, No. 48, pp. 7781-7784, 1993.

"A Versatile Enantiospecific Approach to 3-Azetidinols and Aziridines", Marta Poch, et al., Tetrahedron Letters, vol. 32, No. 47, pp. 6935-6938, 1991.

"Synthesis of 1-Alkyl-3-Hydroxy-2-Phenylazetidines", Takashi Toda, et al., Heterocycles, vol. 33, No. 2, 1992, 511-513.

"Ring Opening of Azetidinols by Phenols: Regiochemistry and Stereochemistry", Robert H. Higgins, et al., J. Org. Chem. 1994, 59, 2172-2178.

"Synthetic Applications of 1-Aminoalkyl Chloromethyl Ketones, Synthesis of Enantiopure 3-Azetidinols and Aminoalkyl Epoxides", Jose Barluenga, et al., J. Org. Chem. 1997, 62, 5974-5977.

"A Human Whole Blood Assay for Clinical Evaluation of Biochemical Efficacy of Cyclooxygenase Inhibitors", C. Brideau, et al., Flamm Res 45:68-74 (1996).

"Reactivos Bioquimicos y Organicos Para Investigation en Biociencias", 2002-2003, Sigma, p. 1222.

"Basic Section, A New and Sensitive Method for Measuring Thermal Nociception in Cutaneous Hyperalgesia", K. Hargreaves, et al., Pain, 32 (1988) 77-88.

"Carrage Induced Edema in Hind Paw of the Rat as an Assay for Antiinflamatory Drugs", Charles A. Winter, et al., Proc. Soc. Exp. Biol. Med. III, 544-547 (1962).

"Selective Inhibition of Cyclooxygenase (COX)-2 Reverses Inflammation and Expression of COX-2 and Interleukin 6 in Rat Adjuvant Arthritis", Gary D. Anderson, et al., J. Clin. Invents, vol. 97, No. 11, Jun. 1996, 2672-2679.

"Effect of Nimesulide on cyclo-oxygenase activity in rat gastric mucosa and inflammatory exudate", O. Tofanetti, et al., Med. Sci. Res., 1989, 17, 745-746.

"New Cyclooxygenase-2/5-Lipoxygenase Inhibitors. 1. 7-tert-Butyl-2,3-dihydro-3,3-dimethylbenzofuran Derivatives as Gastrointestinal Safe Antiinflamatory and Analgesic Agents: Discovery and Variation of the 5-Keto Substituent", John M. Janusz, et al., J. Med. Chem, 1998, 41, 1112-1123.

4 pages of Product Information by Product Number from www.cavmanchem.com product catalog (2004).

"Amberlyst-15($H_+$)-$NaBH_4$-LiGl: An Effective Reductor for Oximes and Hydrazones", Bipul Baruah et al., Synlett 1999, No. 4, 409-410.

* cited by examiner

SUBSTITUTED AZETIDINE COMPOUNDS, THEIR PREPARATION AND USE AS MEDICAMENTS

The present invention relates to substituted Azetidine compounds of general formula (I), methods for their preparation, medicaments comprising these compounds as well as their use for the preparation of a medicament for the treatment of humans and animals.

The metabolites of arachidonic acid, such as prostaglandins, lipoxygenases and thromboxane products are produced in a wide variety of tissues and play a key role in many physiological and pathophysiological processes, such as inflammation, pain and cancer.

Prostaglandins, for example, are produced from cell membrane phospholipids via a cascade of enzymes, involving the conversion of arachidonic acid to a common prostaglandin precursor, $PGH_2$, by the enzyme Cyclooxygenase. Today, two different subtypes of Cyclooxygenase are known, namely Cyclooxygenase-1 (COX-1) and Cyclooxygenase-2 (COX-2).

COX-1, which is not-inducible or modulated by glucocorticoids, is the constitutive cyclooxygenase isoform and is mainly responsible for the synthesis of cytoprotective prostaglandins in the gastrointestinal tract and the synthesis of thromboxane which triggers platelet aggregation in blood platelets. COX-2 is inducible and generally short lived except in the case of certain tumors where it is constitutively activated. COX-2 expression is stimulated in response to endotoxins, cytokines, hormones, growth factors and mitogens.

Thus, the object of the present invention was to provide novel compounds that are particularly suitable as pharmacologically active substances in medicaments. Preferably these compounds should be suitable for inhibition of the Cyclooxygenase-1 and/or Cyclooxygenase-2 and for the prophylaxis and/or treatment of disorders related to these enzymes.

It has surprisingly been found that the substituted compounds of general formula I given below, stereoisomers thereof, corresponding salts and corresponding solvates show inhibition of Cycloxgenase-1 and Cyclooxygenase-2.

Thus, in one of its aspects the present invention relates to substituted azetidine compounds of general formula I,

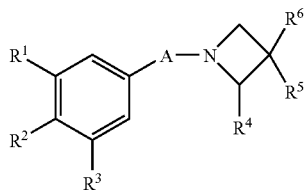

wherein

A represents a —C═O-moiety, a —CH$_2$-moiety, a —CH$_2$—C═O-moiety bonded to the azetidine ring via its carbonyl carbon atom, or a —O—C(═O)-moiety bonded to the azetidine ring via its carbonyl carbon atom, $R^1$, $R^3$, identical or different, represent a hydrogen atom or a linear or branched, saturated or unsaturated, optionally at least mono-substituted $C_{1-4}$-aliphatic group, $R^2$ represents a hydrogen atom, a hydroxyl group or a $C_{1-3}$-alkoxy group, or $R^1$ and $R^2$ or $R^2$ and $R^3$ together form an —O—CH$_2$—CH$_2$-chain, which is optionally substituted with one or more methyl groups, $R^4$ represents a hydrogen atom, an optionally at least mono-substituted aryl group, or a linear or branched, saturated or unsaturated aliphatic group, whereby said aliphatic group may be substituted by one or more substituents independently selected from the group consisting of hydroxy, fluorine, chlorine, bromine, branched or unbranched $C_{1-4}$-alkoxy, branched or unbranched $C_{1-4}$-perfluoroalkoxy and branched or unbranched $C_{1-4}$-perfluoroalkyl, $R^5$ represents a hydrogen atom, a halogen atom, a hydroxyl group, a linear or branched, saturated or unsaturated, optionally at least mono-substituted aliphatic group, an —OR$^7$-moiety, -an —NH$_2$-moiety, a —CO—NH$_2$-moiety, an —NH—CO—R$^8$-moiety, an —N(OH)—CO—NH$_2$-moiety, an —O(CH$_2$)$_{1-4}$ONO$_2$-moiety, an optionally at least mono-substituted aryl group, or a carboxy-group, $R^6$ represent a hydrogen atom, a halogen atom, a hydroxyl group, a linear or branched, saturated or unsaturated, optionally at least mono-substituted aliphatic group, an —OR$^9$-moiety, -an —NH$_2$-moiety, a —CO—NH$_2$-moiety, an —NH—CO—R$^{10}$-moiety, an —N(OH)—CO—NH$_2$-moiety, an optionally at least mono-substituted aryl group, or a carboxy-group, $R^7$, $R^8$, $R^9$, $R^{10}$, independent from one another, represent a linear or branched, saturated or unsaturated, optionally at least mono-substituted aliphatic group, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

It is highly preferred that for the substituted azetidine compounds of general formula I given above one or more of the following provisos (disclaimer) apply, namely that $R^1$, $R^2$ and $R^3$ do not identically represent a hydrogen atom, and if A represents a —CH$_2$-moiety, then at least two of the residues $R^1$, $R^2$ and $R^3$ do not identically represent a hydrogen atom, that if A represents a —(C═O)-moiety, $R^4$ represents a hydrogen atom and one of the residues $R^5$ and $R^6$ represents a hydrogen atom, then the other one of these residues $R^5$ and $R^6$ does not represent an —NH$_2$-moiety, a —CONH$_2$-moiety or a methyl group, which is substituted by an —NH$_2$-moiety or an optionally substituted azaheterocycle, and that if A represents a —(C═O)-moiety, a —CH$_2$C═O-moiety bonded to the azetidine ring via its carbonyl atom, or a —O—C(═O)-moiety bonded to the azetidine ring via its carbonyl carbon atom and one of the residues $R^5$ and $R^6$ represents a hydrogen atom or a linear or branched, saturated or unsaturated, optionally at least mono-substituted aliphatic group, then the other one of these residues $R^5$ and $R^6$ does not represent an —NH$_2$- or -carboxy-moiety, If any of the afore mentioned substituents represents an aliphatic group, which is substituted by one or more substituents, these substituents may, independent from one another, preferably be selected from the group consisting of hydroxy, fluorine, chlorine, bromine, branched or unbranched $C_{1-4}$-alkoxy, branched or unbranched $C_{1-4}$-perfluoroalkoxy, branched or unbranched $C_{1-4}$-perfluoroalkyl, more preferably be selected from the group consisting of hydroxy, F, Cl, Br, methoxy, ethoxy and CF$_3$.

Preferred linear or branched, saturated or unsaturated aliphatic groups, which may be substituted by one or more substituents, may preferably be selected from the group consisting of methyl, ethyl, n-propyl, isopropyl, n-butyl, iso-butyl, sec-butyl, tert-butyl, n-pentyl, n-hexyl, n-heptyl, n-octyl, n-nonyl, n-decyl, vinyl, ethinyl, propenyl, propinyl, butenyl and butinyl.

If any of the afore mentioned substituents represents an aryl group, which is substituted by one or more substituents, these substituents may, independent from one another, preferably be selected from the group consisting of hydroxy, fluorine, chlorine, bromine, branched or unbranched $C_{1-4}$-alkyl, branched or unbranched $C_{2-4}$-alkenyl, branched or unbranched $C_{2-4}$-alkinyl, branched or unbranched $C_{1-4}$-alkoxy, branched or unbranched $C_{1-4}$-perfluoroalkoxy, branched or unbranched $C_{1-4}$-perfluoroalkyl, more preferably be selected from the group consisting of hydroxy, F, Cl, Br, methyl, ethyl, n-propyl, iso-propyl, tert.-Butyl, n-Butyl, sec-Butyl, methoxy, ethoxy and $CF_3$.

Preferred aryl groups, which may optionally be at least mono-substituted, are phenyl and naphthyl.

Preferred are compounds of general formula I given above, wherein $R^1$ and $R^3$, identical or different, represent a hydrogen atom or a linear or branched $C_{1-4}$-alkyl group, preferably $R^1$ and $R^3$ are identical and represent an unsubstituted $C_{1-4}$-alkyl group, more preferably $R^1$ and $R^3$ are identical and represent a $C_{3-4}$ alkyl group, most preferably $R^1$ and $R^3$ are identical and represent an iso-propyl group or a tert.-Butyl group and $R^2$, $R^4$–$R^{10}$ and A have the meaning given above, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

Also preferred are compounds of general formula I given above, wherein $R^2$ represents a hydrogen atom, a hydroxyl group or a methoxy group, and $R^1$, $R^3$–$R^{10}$ and A have the meaning given above, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

Furthermore, compounds of general formula I are preferred, in which $R^4$ represents a hydrogen atom, an optionally at least mono-substituted phenyl group, or a linear or branched, saturated or unsaturated $C_{1-6}$ aliphatic group, whereby said aliphatic group may be substituted with one or more substituents independently selected from the group consisting of hydroxy, fluorine, chlorine, bromine, branched or unbranched $C_{1-4}$-alkoxy, branched or unbranched $C_{1-4}$-perfluoroalkoxy and branched or unbranched $C_{1-4}$-perfluoroalkyl, more preferably $R^4$ a hydrogen atom, a methyl group or an unsubstituted phenyl group and $R^1$–$R^3$, $R^5$–$R^{10}$ and A have the meaning given above, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

Preference is also given to compounds of general formula I given above, in which $R^5$ represents a hydrogen atom, a halogen atom, a hydroxyl group, a linear or branched, saturated or unsaturated, optionally at least mono-substituted $C_{1-6}$ aliphatic group, an —$NH_2$-moiety, a —CO—$NH_2$-moiety, an —NH—CO—$R^8$-moiety, an —N(OH)—CO—$NH_2$-moiety, an —O($CH_2$)$_4$—$ONO_2$-moiety, an optionally at least mono-substituted phenyl group, or a carboxy-group, preferably a hydrogen atom, a bromine atom, a hydroxyl group, an —$NH_2$-moiety, a —CO—$NH_2$-moiety, an —NH—CO—$R^8$-moiety, an —N(OH)—CO—$NH_2$-moiety, —O($CH_2$)$_4$—$ONO_2$-moiety, an unsubstituted phenyl group, or a carboxy-group, and $R^1$–$R^4$, $R^6$–$R^{10}$ and A have the meaning given above, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

Also preferred are compounds of general formula I, in which $R^6$ represents a hydrogen atom, a halogen atom, a hydroxyl group, a linear or branched, saturated or unsaturated, optionally at least mono-substituted $C_{1-6}$ aliphatic group, an —$NH_2$-moiety, a —CO—$NH_2$-moiety, an —NH—CO—$R^8$-moiety, an —N(OH)—CO—$NH_2$-moiety, an optionally at least mono-substituted phenyl group, or a carboxy-group, preferably a hydrogen atom, a hydroxyl group or a methyl group, and $R^1$–$R^5$, $R^7$–$R^{10}$ and A have the meaning given above, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

Preferred are also compounds of general formula I given above, in which $R^7$, $R^8$, $R^9$, $R^{10}$, independent from one another, represent a linear or branched, saturated or unsaturated, optionally at least mono-substituted $C_{1-6}$ aliphatic group, preferably a linear or branched $C_{1-6}$ alkyl group, more preferably a methyl group or an ethyl group, and $R^1$–$R^6$ and A have the meaning given above, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

Particularly preferred are substituted azetidine compounds of general formula I,

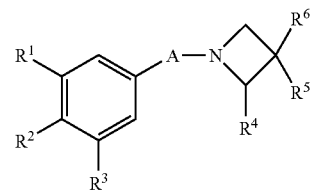

wherein

A represents a —C═O-moiety, a —$CH_2$-moiety, a —$CH_2$—C═O-moiety bonded to the azetidine ring via its carbonyl carbon atom, or a —O—C(═O)-moiety bonded to the azetidine ring via its carbonyl carbon atom, $R^1$, $R^3$ both represent an iso-propyl group or a tert.-butyl group, $R^2$ represents a hydrogen atom, a hydroxyl group or a methoxy group, or $R^1$ and $R^2$ or $R^2$ and $R^3$ together form an —O—$CH_2$—C($CH_3$)$_2$-chain, whereby the oxygen atom of said chain is bonded to the 4-position of the phenyl ring, $R^4$ represents a hydrogen atom, a methyl group or an unsubstituted phenyl group, $R^5$ represents a bromine atom, a hydroxyl group, -an —NH$_2$-moiety, a —CO—NH$_2$-moiety, an —NH—CO—CF$_3$-moiety, an —N(OH)CO—NH$_2$-moiety, an —O(CH$_2$)$_4$ONO$_2$-moiety, an unsubstituted phenyl group, or a carboxy-group, $R^6$ represent a hydrogen atom, a methyl group or a hydroxyl group, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

Most particularly preferred are compounds of general formula I selected from the group consisting of

[1] (3,5-di-tert-butyl-4-hydroxy-phenyl)-(3-hydroxy-azetidin-1-yl methanone;
[2] (3,5-di-tert-butyl-phenyl)-(3-hydroxy-azetidin-1-yl)-methanone;
[3] (3,5-di-tert-butyl-4-hydroxy-phenyl)-(3-hydroxy-3-methyl-azetidin-1-yl)-methanone;
[4] (3,5-di-tert-butyl-4-hydroxy-phenyl)-(3-hydroxy-2-methyl-azetidin-1-yl)-methanone;
[7] (3-Bromo-azetidin-1-yl)-(3,5-di-tert-butyl-4-hydroxy-phenyl)-methanone;
[9] (3,5-di-tert-butyl-4-methoxy-phenyl)-(3-hydroxy-azetidin-1-yl)-methanone;
[10] (3-hydroxy-azetidin-1-yl)-(4-hydroxy-3,5-diisopropyl-phenyl)-methanone;
[11] (3,5-di-tert-butyl-phenyl)-[3-(4-nitrooxy-butoxy)-azetidin-1-yl]-methanone;
[12] (3,5-di-tert-butyl-4-hydroxy-phenyl)-(3-hydroxy-2-phenyl-azetidin-1-yl)-methanone;
[13] (3,5-di-tert-butyl-4-hydroxy-phenyl)-(3-hydroxy-3-phenyl-azetidin-1-yl)-methanone;
[14] (7-tert-butyl-3,3-dimethyl-2,3-dihydro-benzofuran-5-yl)-(3-hydroxy-azetidin-1-yl)-methanone;
[15] [1-(3,5-di-tert-butyl-4-hydroxy-benzyl)-azetidin-3-yl]-N-hydroxy-urea;
[16] N-[1-(3,5-di-tert-butyl-4-hydroxy-benzoyl)-(2S,3R)-2-methyl-azetidin-3-yl]-2,2,2-trifluoro-acetamide;
[17] 1-(3,5-di-tert-butyl-4-hydroxy-benzyl)-azetidin-3-ol;
[18] 2-(3,5-di-tert-butyl-4-hydroxy-phenyl)-1-(3-hydroxy-azetidin-1-yl)-ethanone;
[19] (3-hydroxy-azetidine-1-carboxylic acid)-3,5-di-tert-butyl-phenyl ester
optionally in form of a corresponding salt or a corresponding solvate.

In another aspect the present invention relates to a process for the preparation of the inventive substituted azetidine compounds of general formula I given above, according to which at least one compound of general formula II,

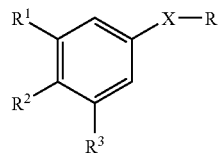

wherein $R^1$–$R^3$ have the meaning given above, X represents a bond or an —(CH$_2$)-moiety and R represents a carboxy group or an activated carbonyl group, is reacted with at least one compound of general formula III,

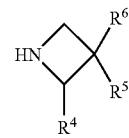

optionally in the form of a corresponding salt, wherein $R^4$–$R^6$ have the meaning given above, to yield a compound of general formula I given above, wherein $R^1$ to $R^6$ have the meaning given above and A represents a —(C═O)-moiety or a —(CH$_2$—CO-moiety, which is optionally purified and/or optionally isolated, and optionally at least one compound of general formula I, wherein A represents a —(C═O)-moiety is reduced to yield at least one compound of general formula I, wherein $R^1$–$R^6$ have the meaning given above and A represents a —(CH$_2$)-moiety, which is optionally purified and/or optionally isolated, or at least one compound of general formula IV,

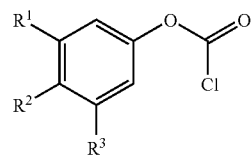

wherein $R^1$–$R^3$ have the meaning given above, is reacted with at least one compound of general formula III given above, to yield at least one compound of general formula I, wherein $R^1$–$R^6$ have the meaning given above and A represents an O—(C═O)-moiety, and said compound is optionally purified and/or optionally isolated.

Compounds of general formula (II) may be prepared by conventional methods known to those skilled in the art.

The reaction of compounds of general formula (II) and general formula (III) may also be carried out according to conventional methods well known to those skilled in the art. The compounds of general formula II may either be used in form of the free carboxylic acid, i.e. R represents a —COOH group, or in form of an activated carbonyl group. Suitable activating groups and methods for activation are well-known to those skilled in the art, e.g. activation with N,N-Dicyclohexylcarbodiimide or other coupling reagents.

The reaction between compounds of of general formula II and compounds of general formula III is preferably carried out in a suitable reaction medium such as diethyl ether, tetrahydrofuran, dioxane, dimethoxyethane and the like. Reaction temperatures and reaction times may vary over a broad range. The temperature is preferably kept in the range of ambient temperature, i.e. approximately 25° C. and the boiling point of the reaction medium. Suitable reaction times may vary over a broad range, i.e. from a few minutes to several hours.

Other compounds of general formula II, wherein R represents an activated carbonyl group include but are not limited to the acide chlorides, anhydrides, mixed anhydrides, alkyl esters, preferably C$_{1-4}$ alkyl esters or activated ester, e.g. p-nitro-phenyl esters.

If the activated compound of general formula II is an acid chloride it is preferably prepared by conventional methods well known to those skilled in the art, e.g. by reaction of the respective compound of general formula II in form of the free carboxylic acid with thionyl chloride or oxalyl chloride, whereby said chlorinating agent may also be used as the reaction medium, optionally in a mixture with at least one other reaction medium. Other suitable reaction media include but are not limited thereto hydrocarbons such as benzene, toluene or xylene, halogenated hydrocarbons such as methylenechloride, chloroform or carbon tetrachloride, or ethers such as diethyl ether, dioxane, tetrahydrofuran or dimethoxyethane or mixtures of two or more of these afore mentioned compounds. Suitable reaction temperatures and reaction times may vary over a broad range, for example, from 0° C. to the boling point of the reaction medium and from several minutes to several hours.

The reaction of an acid chloride of general formula II with an azetidine compound of general formula III is preferably carried out in the presence of inorganic base such as sodium hydroxide, potassium hydroxide, sodium carbonate, potassium carbonate and the like and/or in the presence of an organic base such as triethyl amine, pyridine and the like in a suitable reaction medium such as a hydrocarbons like benzene, toluene or xylene, halogenated hydrocarbons like methylenechloride, chloroform or carbon tetrachloride, or ethers such as diethyl ether, dioxane, tetrahydrofuran or dimethoxyethane or mixtures of at least two or more of the afore mentioned compounds. Said reaction may also be carried out in a reaction medium based on one or more of the afore mentioned compounds and water in a biphasic system.

Those skilled in the art understand that if the compound of general formula II is present in the form of an acid chloride and compound of general formula III is substituted with one or two hydroxyl groups in the 3-position of the azetidine ring, then reaction may also take place between the acid chloride and said alcohol group(s). In this case, the compound of general formula I may be obtained via selective hydrolysis of the respective ester by reaction with a suitable base, preferably lithium hydroxide, in a water-based reaction medium, whereby the reaction medium may comprise conventional organic solvents, which are partially or totally miscible with the aqueous phase, such as methanol, ethanol, propanol and the like or a suitable ether such as tetrahydrofuran, dioxane or dimethoxyethane. Reaction temperature and reaction time may vary over a broad range, preferably from −20° C. to ambient temperature, i.e. approximately 25° C. and from several hours to several days.

If the activated derivative of general formula is a mixed anhydride said compound may preferably be prepared by reaction of the corresponding free acid with an alkyl chloroformiate or an aryl chloroformiate compound, preferably in the presence of a base such as triethylamine or pyridine in a suitable reaction medium.

The compounds of general formula I, wherein A represents a —(C=O)-moiety, may be reduced to the corresponding compound of general formula I, wherein A represents a —(CH$_2$)-moiety, using at least one suitable reducing agent known to those skilled in the art. A preferred reducing agent is lithium aliuminium hydride. Those skilled in the art understand that if the respective compound of general formula I, wherein A represents a —(C=O)-moiety contains one or more further groups, which are suceptible to reduction, these will also be reduced and suitable steps of protecting these groups may be required.

The reduction is preferably carried out in a suitable reaction medium such as ether, preferably diethyl ether, tetrahydrofurane, dioxane or dimethoxyethane. The reaction temperature and reaction time may vary over a broad range, e.g. from ambient temperature, i.e. approximately 25° C. to the boiling point of the reaction medium and from several minutes to several hours.

The compounds of general formula IV may preferably be prepared from compounds of general formula V,

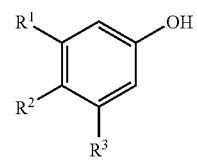

wherein $R^1$–$R^3$ have the meaning given above, by reaction with diphosgene in an anhydrous solvent such as ether, preferably diethyl ether, tetrahydrofuran, dioxane, dimethoxyethan and the like. Reaction temperatures may vary over a broad range, whereby preferred temperatures range from −20° C. to ambient temperature, i.e. approximately 25° C. and suitable reaction times vary from several minutes to several hours.

The reaction of compounds of general formula IV with compounds of general formula III may preferably be carried out in the presence of an organic base such triethylamine, pyridine and the like in a suitable reaction medium such as hydrocarbons like benzene, toluene, xylene, halogenated hydrocarbons like methylene chloride, chloroform, or carbontetrachloride, ethers like diethyl ether, tetrahhydrofuran or dimethoxyethan or mixtures of at least two of these afore mentioned solvents. Reaction temperatures and reaction times may vary over a broad range, preferably from 0° C. to the boiling point of the reaction medium and from several minutes to several hours.

The substituted azetidine compounds of general formula III may be prepared by conventional methods described in the prior art, for example in V. R. Gaertner, J. Org. Chem., 1967, 32, 2972; A. G. Anderson et al., J. Org. Chem., 1972, 37, 3953; N. H. Cromwell et al., Chem. Rev., 1979, 79, 331–358; D. Nisato et al., J. Heterocyclic Chem., 1985, 22, 961–963; A. P. Kozikowski et al., Synlett, 1991, 783–784; J. Frigola et al., J. Med. Chem., 1993, 36, 801–810; J. Frigola et al., J. Med. Chem., 1994, 37, 4195–4210; J. Frigola et al., J. Med. Chem., 1995, 38, 1203–1215; M. Poch et al., Tetrahedron Letters, 1993, 34 (48), 7781–7784; M. Poch et al., Tetrahedron Letters, 1991, 32 (47), 6935–6938; T. Toda et al., Heterocycles, 1992, 33, 511–514; R. H. Higgins et al., J. Org. Chem., 1994, 59, 2172–2178; J. Barluenga et al., J. Org. Chem., 1997, 62, 5974–5977; U.S. Pat. No. 5,073,646 and references cited therein. The respective parts of the description are hereby enclosed by reference and form part of the present disclosure.

In a further aspect the present invention also provides a process for the preparation of salts of substituted azetidine compounds of general formula (I), or stereoisomers thereof, wherein at least one compound of general formula (I) having at least one basic group is reacted with at least one inorganic and/or organic acid, preferably in the presence of a suitable reaction medium. Suitable reaction media include, for example, any of the ones given above. Suitable inorganic acids include hydrochloric acid, hydrobromic acid, phosphoric acid, sulfuric acid, nitric acid, suitable organic acids are e.g. citric acid, maleic acid, fumaric acid, tartaric acid, or derivatives thereof, p-toluenesulfonic acid, methanesulfonic acid or camphersulfonic acid.

In yet a further aspect the present invention also provides a process for the preparation of salts of substituted azetidine compounds of general formula (I), or stereoisomers thereof, wherein at least one compound of general formula (I) having at least one acidic group is reacted with one or more suitable bases, preferably in the presence of a suitable reaction medium. Suitable bases are e.g. hydroxides, carbonates or alkoxides, which include suitable cations, derived e.g. from alkaline metals, alkaline earth metals or organic cations, e.g. $[NH_nR_{4-n}]^+$, wherein n is 0, 1, 2, 3 or 4 and R represents a branched or unbranched $C_{1-4}$-alkyl-radical. Suitable reaction media are, for example, any of the ones given above.

Solvates, preferably hydrates, of the substituted azetidine compounds of general formula (I), of corresponding stereoisomers, or of corresponding salts thereof may also be obtained by standard procedures known to those skilled in the art.

The purification and isolation of the inventive substituted azetidine compounds of general formula (I), of a corresponding stereoisomer, or salt, or solvate or any intermediate thereof may, if required, be carried out by conventional methods known to those skilled in the art, e.g. chromatographic methods or recrystallization.

If the substituted azetidine compounds of general formula (I) themselves are obtained in form of a mixture of stereoisomers, particularly enantiomers or diastereomers, said mixtures may be separated by standard procedures known to those skilled in the art, e.g. chromatographic methods or fractunalized crystallization with chiral reagents. It is also possible to obtain pure stereoisomers via stereoselective synthesis.

The substituted azetidine compounds of general formula (I), their stereoisomers, corresponding salts thereof and corresponding solvates are toxicologically acceptable and are therefore suitable as pharmaceutical active substances for the preparation of medicaments.

It has surprisingly been found that the substituted compounds of general formula I given above, stereoisomers thereof, corresponding salts and corresponding solvates show inhibition of Cyclooxgenase-1 and/or Cyclooxygenase-2.

Thus, in another aspect the present invention relates to a medicament comprising at least one substituted azetidine compound of general formula I given above, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof, and optionally one or more pharmaceutically acceptable excipients.

Preferably the medicament of the present invention is suitable for the inhibition of Cyclooxygenase-1, for the prophylaxis and/or treatment of Cyclooxygenase-1 related disorders, for the inhibition of Cyclooxygenase-2 and/or for the prophylaxis and/or treatment of Cyclooxygenase-2 related disorders.

Particularly preferably the medicament of the present invention is suitable for the prophylaxis and/or treatment of pain, for the prophylaxis and/or treatment of inflammation and/or for the prophylaxis and/or treatment of inflammation related disorders, whereby said inflammation-related disorders may preferably be selected from the group consisting of arthritis, rheumatoid arthritis, spondyloarthropathies, gouty arthritis, osteoarthritis, systemic lupus erythematosus, juvenile arthritis, rheumatic fever, symptoms associated with influenza or other viral infections, common cold, lower back pain, neck pain, dysmenorrhea, headache, toothache, sprains, strains, myositis, neuralgia, synovitis, gout, ankylosing spondylitis, bursitis, edema, inflammations following dental procedures, inflammations following dental procedures, vascular diseases, migraine headaches, periarteritis nodosa, thyroiditis, aplastic anemia, Hodkin's disease, sclerodoma, type I diabetes, myasthenia gravis, sarcoidosis, nephrotic syndrome, Behcet's syndrome, polymyositis, gingivitis, hypersensivity, conjunctivitis, swelling ocurring after injury and myocardia ischemia, for the prophylaxis and/or treatment of asthma, for the prophylaxis and/or treatment of bronchitis, for the prophylaxis and/or treatment of tendinitis, for the prophylaxis and/or treatment of bursitis, for the prophylaxis and/or treatment of skin related conditions, whereby said skin related conditions may preferably be selected from the group consisting of psoriasis, eczema, burns and dermatitis, for the prophylaxis and/or treatment of gastrointestinal disorders, whereby said gastrointestinal disorders may preferably be selected from the group consisting of inflammatory bowel disease, Crohn's disease, gastritis, irritable bowel syndrome and ulcerative colitis, or for treatment of fever, or for the prophylaxis and/or treatment of cancer or a cancer-related disorders, whereby said cancer or related disorder may preferably be selected from the group consisting of brain cancer, bone cancer, epithelial cell-derived neoplasia (epithelial carcinoma), basal cell carcinoma, adenocarcinoma, gastrointestinal cancer, lip cancer, colon cancer, liver cancer, bladder cancer, pancreas cancer, ovary cancer, cervical cancer, lung cancer, breast cancer, skin cancer, squamous cell cancer, prostate cancer, renal cell carcinoma and other known cancers that effect epithelial cells throughout the body, for the prophylaxis and/or treatment of polyps, for the prophylaxis and/or treatment of angiogenesis mediated disorders, preferably selected from the group consisting of metastasis, corneal graft rejection, ocular neovascularization, retinal neovascularisation, diabethic retinopathy, retrolental fibroplasia, neovascular glaucoma, gastric ulcer, infantile hemaginomas, angiofibroma of the nasopharynx, avascular necrosis of the bone and endometriosis.

Most particularly preferred the medicament of the present invention is suitable for the prophylaxis and/or treatment of pain, for the prophylaxis and/or treatment of inflammation and/or for the prophylaxis and/or treatment of inflammation related disorders, whereby said inflammation-related disorders may preferably be selected from the group consisting of arthritis, rheumatoid arthritis, spondyloarthropathies, gouty arthritis, osteoarthritis, systemic lupus erythematosus, juvenile arthritis, rheumatic fever, symptoms associated with influenza or other viral infections, common cold, lower back pain, neck pain, dysmenorrhea, headache, toothache, sprains, strains, myositis, neuralgia, synovitis, gout, ankylosing spondylitis, bursitis, edema, inflammations following dental procedures, inflammations following dental procedures, vascular diseases, migraine headaches, periarteritis nodosa, thyroiditis, aplastic anemia, Hodkin's disease, sclerodoma, type I diabetes, myasthenia gravis, sarcoidosis, nephrotic syndrome, Behcet's syndrome, polymyositis, gingivitis, hypersensivity, conjunctivitis, swelling ocurring after injury and myocardia ischemia.

In yet another aspect the present invention relates to the use of at least one substituted azetidine of general formula I given above, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof, optionally in combination with one or more pharmaceutically acceptable excipients, for the preparation of a medicament for the inhibition of Cyclooxygenase-1, for the prophylaxis and/or treatment of Cyclooxygenase-1 related disorders, for the inhibition of Cyclooxgenase-2 and/or for the prophylaxis and/or treatment of Cyclooxygenase-2 related disorders.

The use of at least one substituted azetidine compound of general formula I given above, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof, optionally in combination with one or more pharmaceutically acceptable excipients, for the preparation of a medicament for the prophylaxis and/or treatment of pain, for the prophylaxis and/or treatment of inflammation and/or for the prophylaxis and/or treatment of inflammation related disorders, whereby said inflammation-related disorders may preferably be selected from the group consisting of arthritis, rheumatoid arthritis, spondyloarthropathies, gouty arthritis, osteoarthritis, systemic lupus erythematosus, juvenile arthritis, rheumatic fever, symptoms associated with influenza or other viral infections, common cold, lower back pain, neck pain, dysmenorrhea, headache, toothache, sprains, strains, myositis, neuralgia, synovitis, gout, ankylosing spondylitis, bursitis, edema, inflammations following dental procedures, inflammations following dental procedures, vascular diseases, migraine headaches, periarteritis nodosa, thyroiditis, aplastic anemia, Hodkin's disease, sclerodoma, type I diabetes, myasthenia gravis, sarcoidosis, nephrotic syndrome, Behcet's syndrome, polymyositis, gingivitis, hypersensivity, conjunctivitis, swelling ocurring after injury and myocardia ischemia, for the prophylaxis and/or treatment of asthma, for the prophylaxis and/or treatment of bronchitis, for the prophylaxis and/or treatment of tendinitis, for the prophylaxis and/or treatment of bursitis, for the prophylaxis and/or treatment of skin related conditions, whereby said skin related conditions may preferably be selected from the group consisting of psoriasis, eczema, burns and dermatitis, for the prophylaxis and/or treatment of gastrointestinal disorders, whereby said gastrointestinal disorders may preferably be selected from the group consisting of inflammatory bowel disease, Crohn's disease, gastritis, irritable bowel syndrome and ulcerative colitis, or for treatment of fever, or for the prophylaxis and/or treatment of cancer or a cancer-related disorders, whereby said cancer or related disorder may preferably be selected from the group consisting of brain cancer, bone cancer, epithelial cell-derived neoplasia (epithelial carcinoma), basal cell carcinoma, adenocarcinoma, gastrointestinal cancer, lip cancer, colon cancer, liver cancer, bladder cancer, pancreas cancer, ovary cancer, cervical cancer, lung cancer, breast cancer, skin cancer, squamous cell cancer, prostate cancer, renal cell carcinoma and other known cancers that effect epithelial cells throughout the body, for the prophylaxis and/or treatment of polyps, for the prophylaxis and/or treatment of angiogenesis mediated disorders, preferably selected from the group consisting of metastasis, corneal graft rejection, ocular neovascularization, retinal neovascularisation, diabethic retinopathy, retrolental fibroplasia, neovascular glaucoma, gastric ulcer, infantile hemaginomas, angiofibroma of the nasopharynx, avascular necrosis of the bone and endometriosis is particularly preffered.

The use of at least one substituted azetidine compound of general formula I given above, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof, optionally in combination with one or more pharmaceutically acceptable excipients, for the preparation of a medicament for the prophylaxis and/or treatment of pain, for the prophylaxis and/or treatment of inflammation and/or for the prophylaxis and/or treatment of inflammation related disorders, whereby said inflammation-related disorders may preferably be selected from the group consisting of arthritis, rheumatoid arthritis, spondyloarthropathies, gouty arthritis, osteoarthritis, systemic lupus erythematosus, juvenile arthritis, rheumatic fever, symptoms associated with influenza or other viral infections, common cold, lower back pain, neck pain, dysmenorrhea, headache, toothache, sprains, strains, myositis, neuralgia, synovitis, gout, ankylosing spondylitis, bursitis, edema, inflammations following dental procedures, inflammations following dental procedures, vascular diseases, migraine headaches, periarteritis nodosa, thyroiditis, aplastic anemia, Hodkin's disease, sclerodoma, type I diabetes, myasthenia gravis, sarcoidosis, nephrotic syndrome, Behcet's syndrome, polymyositis, gingivitis, hypersensivity, conjunctivitis, swelling ocurring after injury and myocardia ischemia is most particularly preferred.

The medicament according to the present invention may be in any form suitable for the application to humans and/or animals, preferably humans including infants, children and adults and can be produced by standard procedures known to those skilled in the art. The composition of the medicament may vary depending on the route of administration.

The medicament of the present invention may for example be administered parentally in combination with conventional injectable liquid carriers, such as water or suitable alcohols. Conventional pharmaceutical excipients for injection, such as stabilizing agents, solubilizing agents, and buffers, may be included in such injectable compositions. These medicaments may for example be injected intramuscularly, intraperitoneally, or intravenously.

Medicaments according to the present invention may also be formulated into orally administrable compositions containing one or more physiologically compatible carriers or excipients, in solid or liquid form. These compositions may contain conventional ingredients such as binding agents, fillers, lubricants, and acceptable wetting agents. The compositions may take any convenient form, such as tablets, pellets, granules, capsules, lozenges, aqueous or oily solutions, suspensions, emulsions, or dry powdered forms suitable for reconstitution with water or other suitable liquid medium before use, for immediate or retarded release.

The liquid oral forms for administration may also contain suitable additives such as sweeteners, flavoring, preservatives, and emulsifying agents. Non-aqueous liquid compositions for oral administration may also be formulated, containing edible oils. Such liquid compositions may be conveniently encapsulated in e.g., gelatin capsules in a unit dosage amount.

The compositions of the present invention may also be administered topically or via a suppository.

The daily dosage for humans and animals may vary depending on factors that have their basis in the respective species or other factors, such as age, sex, weight or degree of illness and so forth. The daily dosage for humans may preferably be in the range from 1 to 2000, preferably 1 to 1500, more preferably 1 to 1000 milligrams of active substance to be administered during one or several intakes per day.

Pharmacological Methods:

I. Cox-1/Cox-2 Enzyme Assay:

The Cox-1/Cox-2 enzyme assay for the inventive azetidine compounds is carried out according to the following description:

Approximately 390 units of the Cox-1 or Cox-2 enzyme (Cayman Chemical, Ann Habor, Mich., U.S.A., catalogue number 60100 and 60120 respectively are suspended in 200–300 µl of Tris HCl (100 mM), hematin (1 mM) and phenol (2 mM) buffer, and 200 ml epinephrine (5.8 mM) as chromogen. The compounds, which are to be tested, are solved in dimethylformamide or 0.1 N sodium hydroxide, at a volume of 60 µl. The total volume of each enzyme reaction is 0.6 ml. It is taken care that the vehicle concentration in the reaction mixture does not exceed 5% (volume/volume). The reaction medium is incubated for 4 minutes at 37° C., and then 100 µl of 0.5 mM arachidonic acid are added as substrate.

Immediately after the addition of the substrate, the slope corresponding to the optical density increase at 480 nm is recorded for 1 minute. The reaction is monitored with a Hewlett-Packard 8452A spectrophotometer.

II. Determination of Cox-1- and Cox-2-Activity in Human Whole Blood

The Cox-1- and Cox-2-activity in human whole blood is determined according to a modification of the method described in the publication of C. Brideau et al., "A human whole blood assay for clinical evaluation of biochemical efficacy of cyclooxygenase inhibitors", Inflamm Res 1996; 45: 68–74. The respective part of the description is hereby incorporated by reference and forms part of the present disclosure.

For Cox-1 activity determination, fresh human blood is distributed in a volume of 0.5 ml to silicone Eppendorf tubes, into which 2 µl of the compound to be tested or dimethylsulfoxide (DMSO) at a final concentration of 0.4% (volume/volume). The tubes are inverted for homogenization and incubated for 1 hour at 37° C. under slight stirring. Afterwards they are centrifuged for 15 min at 10500 g and 100 µl of serum is collected. Proteins are precipitated by the addition of 400 µl of methanol to each tube, tubes were centrifuged for 10 minutes at 5000 g and 300 µl of supernatant is aspirated and then dried under nitrogen atmosphere.

Tromboxane B2 (TXB2) concentration is quantified using an assay kit (Caymann Chemical, Ann Arbor, Mich., U.S.A., Catalogue number 519031) after reconstitution into 300 µl assay buffer supplied in the assay kit.

For Cox-2 activity determination, tubes are prepared with 2 µl of the compound to be tested or DMSO, 12 µg/ml of aspirine, 9 µl of 1% (weight/volume) sodium heparine and 0.5 ml of fresh human blood. Samples are pre-incubated at 37° C. during 15 minutes and *E. coli* 0111:B4 LPS (from Sigma Chemical, St. Louis, Mo., U.S.A., catalogue number L-3012) are added for incubation during 24 h at 37° C. The samples are centrifuged for 100 µl of plasma collection. 400 µl of Ethyl acetate and 1% (volume/volume) methanol are added to each sample and the tubes are stirred and centrifuged for 10 minutes at 5000 g at 4° C. 300 µl of supernatant are aspirated and evaporated under nitrogen atmosphere.

Prostaglandin E2 concentration is quantified using an assay kit from Cayman Chemical, Ann Arbor, Mich., U.S.A. (Catalogue number: 514010) after reconstitution into 300 µl assay buffer supplied in the assay kit.

III: Analgesia Test in Rats

The inventive compounds are tested for analgesic activity as described above is carried out as described in the publication of K. Hargreaves et al., Pain, 32, 77–88, (1988). The respective part of the description is hereby incorporated by reference and forms part of the disclosure.

The rats are transferred to the experimentation laboratory, where they remain in groups of 5, in makrolon cages with a barred floor to avoid coprophagy. At the beginning of the experiment, water and food were removed, and animals were adequately weighed and marked.

Each rat receives via subplantar injection 0.1 ml of sterile saline solution into the left hind paw, followed by 0.1 ml of a 2% (weight/volume) carrageenan suspension in sterile saline solution into the right hind paw.

Two hours after the subplantar injections of carrageenan and vehicle, each rat receives by oral route the compounds to be tested, suspended in 5% (weight/volume) gum arabic, administered at 10 ml per kg of body weight.

Two hours after the administration of the compounds to be tested, the values for analgesic activity are determined. To this purpose, the rats are transferred to the methacrylate chambers of an analgesimeter provided with a glass floor. Once the acclimatisation period in the chambers is over (i.e. after 5 minutes) an infra-red beam lamp capable of producing a thermal stimulus, is placed below the rat's paws.

The thermal stimulus, previously calibrated at 10 Amperes, is applied to each of the hind paws with at least 1 minute intervals. The response of the rats to pain consists of raising the paw, thus avoiding contact with the floor. Simultaneously, the infra-red light is automatically turned down, and the digital display of the device shows the latency time in seconds. The rats are tested once only to avoid possible learning behaviour.

IV. Test for Activity Against Edema in Rats

The test for activity against edema is carried out as described in the publication of Winter et al., Proc. Soc. Exp. Biol. Med. 111, 544–547, (1962). The respective part of the description is hereby incorporated by reference and forms part of the present disclosure.

At the beginning of each experimental session the rats are deprived of food, and kept in cages within groups of 5 animals, the cages being fitted with a grating on the floor to prevent coprophagy. After a period of 24 hours without food, the animals are marked in a suitable way, weighed and hydrated via oral administration of 30 ml/kg body weight of tap water. Half an hour after the hydratisation, the compounds to be tested are administered via oral route, in an amount of 10 ml/kg body weight as a suspension in gum arabic at 5% (weigh/volume). One hour after administration of the compounds the animals receive 0.1 ml of the inflammation causing agent (carrageenin 1% weight/volume, in sterile solution), injected via subplantar route into the right hind paw of the rats. Immediately after the carrageenin injection the volume of the injected paw is determined using a plethysmometer. The readings are expressed in ml. Readings of the volume of the paw are taken every hour after administration of the carrageenin for 7 hours.

V: Test for Antiarthritic Activity in Rats

The test for antiarthritic activity is carried out as described in the publication of Anderson et al., J. Clin. Invest. 97, 11, 2672–2679, (1996). The respective part of the description is hereby incorporated by reference and forms part of the present disclosure.

On day 0 of the experiment, the volumes of the contralateral paws to those injected, i.e. left hind paws, are measured by means of a pletismometer, the readings of which are expressed in ml.

Next, each rat is injected the adjuvant, consisting of 1 mg of *Mycobacterium butyricum* suspended in 0.1 ml of mineral oil, via subplantar route in the right hind paw.

Approximately every day, and for 15 days after the injection of adjuvant, the volumes of non-injected hind paws (contralateral) are measured again. On day 15, those rats of which the contralateral paws show an increase of at least 0.42 ml compared to the day of the adjuvant injection are selected, discarding those animals with lower volume increases, since their inflammation is not considered to have the adequate magnitude.

On day 15 of the experiment, daily administration of the compounds to be tested via oral route is started, and on each day, the volumes of non-injected hind paws is recorded.

On Day 25 of the experiment, the body weights and non-injected hind paws (contralateral) volumes are measured for the last time, and these values were used to determine the activities.

VI: PGE2 Production in Rat Inflammatory Exudate and Gastric Mucosa

The PGE2 production in rat inflammatory exudate and gastric mucosa is carried out as described in the publication of O Tofanetti et al., "Effect of nimesulide on cyclooxygenase activity in rat gastric mucosa and inflammatory exudate", Med Sci Res 17, 745–746 (1989). The respective part of the description is hereby incorporated by reference and forms part of the present disclosure.

For this text 6 male wistar rats (Interfauna-St Feliú de Codines, Barcelona) of approximately 200 g (each approximately 6 weeks of age) are used. The compounds to be tested are administered via oral route in gum Arabic at 5% (weight/volume) at a rate of 10 ml/kg.

One hour after administration of the compounds and under halothane anaesthesia, each rat is implanted subcutaneously in the interescapular area a 40×15×5 mm polyester sponge, soaked in a 0.5% suspension of carrageenan. Rats are sacrificed 6 hours after the implant, the sponges are removed and squeezed. The exudates are collected and centrifuged at 6000×G for 15 minutes.

The rats's stomachs are removed and the gastric mucosa is detached from the underlying layers and by means of a 10 mm diameter die, mucosa samples from an area between the gastric corpus and pyloric antrum are taken. The mucosal PGE2 is extracted. PGE2 concentrations from the inflammatory exudates and the gastric mucosa are determined by means of immunoassay reagents of Cayman Chemical kit, Ann Arbor, Mich., U.S.A. (Catalogue number: 514010) according to the manufacturer's instructions.

The present invention is illustrated below with the aid of examples. These illustrations are given solely by way of example and do not limit the general spirit of the present invention.

EXAMPLES

Example 1

Synthesis of (3,5-di-tert-butyl-4-hydroxy-phenyl)-(3-hydroxy-azetidin-1-yl)-methanone a) 3,5-Di-tert-butyl-4-hydroxy-benzoyl chloride

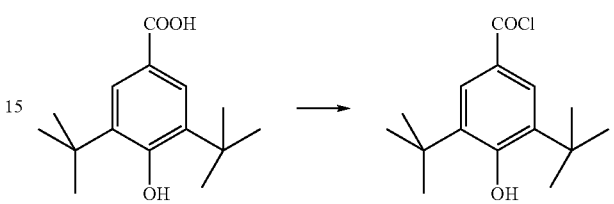

3,5-Di-tert-butyl-4-hydroxy-benzoic acid (16,6 g, 66,3 mmoles) was dissolved in chloroform (150 ml) and Thionyl chloride (10 ml, ≈139 mmoles) was added. The resulting mixture was refluxed for 9 hours, cooled to room temperature (approximately 25° C.) and evaporated to dryness under reduced pressure. 17,6 g (99% of theoretical yield) of 3,5-di-tert-butyl-hydroxy-benzoyl chloride were obtained in form of yellow solid, which was used in the following reaction step without purification.

IR (KBr, cm$^{-1}$): 3555, 2958, 1736, 1125.

b) (3,5-Di-tert-butyl-4-hydroxy-phenyl)-(3-hydroxy-azetidin-1-yl)-methanone

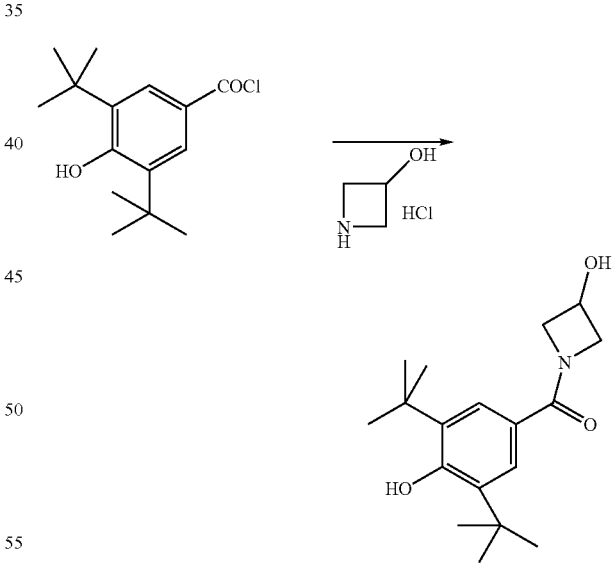

Azetidin-3-ol hydrochloride (2 g, 18,3 mmoles) was dissolved in a 5% weight/weight (45 ml) of an aqueous solution of sodium hydroxide, the resulting solution cooled to −5° C. and under vigorous stirring 3,5-di-tert-butyl-4-hydroxy-benzoyl chloride (5,4 g, 20 mmoles) obtained according to step (a) dissolved in 8 ml of THF was added. Afterwards the cooling bath was removed, the reaction mixture warmed to room temperature (approximately 25° C.) and stirred for an additional hour under these conditions. The reaction mixture was then extracted several times with diethyl ether, the etherical phases combined, washed with water, dried with sodium sulfate and evaporated to dryness to obtain 1,9 g of the crude product, which is crystallized from ethyl acetate-petroleum ether. 1,6 g (30% of theoretical yield) of (3,5-di-tert-butyl-4-hydroxy-phenyl)-(3-hydroxy-azetidin-1-yl)-methanone were obtained in crystalline form.

Melting point=185–189° C. IR (KBr, cm$^{-1}$): 3506, 3262, 2956, 1611, 1572, 1449, 1421, 1406, 1113. $^1$H-NMR (CDCl$_3$, δ): 1,43 (s, 18H), 2,8 (bs, 1H), 4,0–4,2 (m, 2H), 4,45 (m, 2H), 4,7 (m, 1H), 5,5 (s, 1H), 7,5 (s, 2H).

Example 3

(3,5-di-tert-butyl-hydroxy-phenyl)-(3-hydroxy-3-methyl-azetidin-1-yl)-methanone

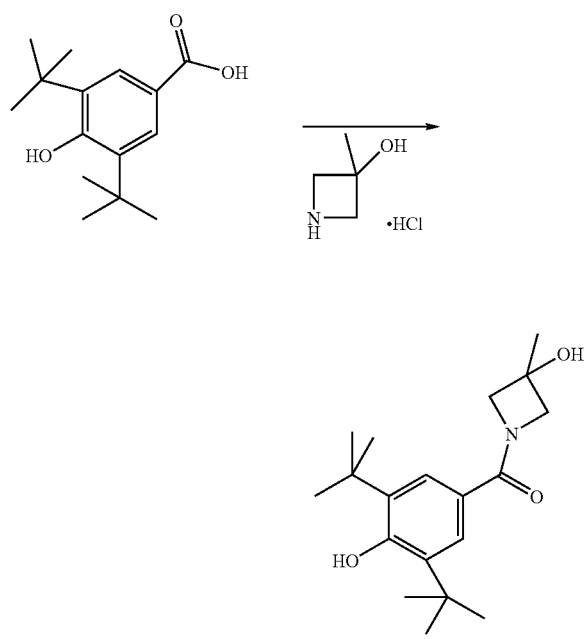

3-Methyl-azetidin-3-ol hydrochloride (0,6 g, 4,84 mmoles) was suspended in tetrahydrofuran (50 ml) and Triethylamine (1,2 ml) was added. The mixture was stirred at room temperature (approximately 25° C.) for 30 minutes and 3,5-di-tert-butyl-4-hydroxy benzoic acid (1,26 g, 5,1 mmoles) was added in one portion, the mixture was cooled to 0° C. and subsequently a solution of dicyclohexylcarbodiimide (1 g, 4,84 mmoles) in tetrahydrofuran (27 ml) was added. The reaction mixture was then heated to reflux for 3,5 hours, cooled and the insoluble solid was filtered off. The filtrate was concentrated using a rotavapor, the remaining solid dissolved in ethyl acetate, washed with water, dried over magnesium sulfate, filtered and evaporated to dryness. The crude residue obtained is crystallized from diethyl ether to give 1,14 g (73% of theoretical yield) of (3,5-di-tert-butyl-4-hydroxy-phenyl)-(3-hydroxy-3-methyl-azetidin-1-yl)-methanone.

Melting point=148–153° C. IR (KBr, cm$^{-1}$): 3497, 3274, 2963, 1612, 1598, 1415, 1235, 1120. $^1$H-NMR (CDCl$_3$, δ): 1,4 (s, 18H), 1,5 (s, 3H), 3,9 (s, 1H), 4,1 (m, 3H), 4,3 (m, 1H), 5,5 (s, 1H), 7,5 (s, 2H).

Example 15

Synthesis of [1-(3,5-di-tert-butyl-4-hydroxy-benzyl)-azetidin-3-yl]-N-hydroxy-urea (a) [1-(3,5-Di-tert-butyl-4-hydroxy-benzyl)-azetidin-3-yl]-N-hydroxy-carbamic acid phenyl ester 1-(3,5-di-tert-butyl-4-hydroxy-benzyl)-azetidin-3-ol (2,27 g, 7,8 mmols), N,O bis-(phenoxycarbonyl)hydroxylamino (2,36 g, 8,58 mmols) (prepared according to the method described in A. O. Stewart and D. W. Brooks, J. Org. Chem., 57(18), 1992, 5020–5023. The respective part of the description is introduced by reference and forms part of the disclosure), and Triphenylphosphine (2,45 g, 9.36 mmols) were dissolved in 80 ml of anhydrous Tetrahydrofurane. The reaction mixture was cooled to 0° C. under a nitrogen atmosphere, a solution of diisopropylazodicarboxylate (1,84 ml, 9.36 mmols) was added dropwise and the mixture was stirred at 0° C. for one hour. Afterwards the mixture was allowed to warm up to room temperature and stirred overnight. The solvent was removed under reduced pressure via a rotavapor and the crude product was purified via column chromatography (silica gel, eluent: CHCl$_3$). After crystallization from diethyl ether 1,53 g (46% of theoretical yield) of the desired product were obtained as a white solid having a melting point of 161–163° C.

IR (KBr, cm$^{-1}$) 3540, 3420, 2958, 1720, 1440, 1198, 760 $^1$H-NMR (CDCl$_3$, δ): 1,4 (s, 18H), 3,5 (t, 2H), 3,6 (m+s, 4H), 4,75 (m, 1H), 5,2 (bs, 1H), 7,05 (m, 3H), 7,25 (d, 1H), 7,3 (m, 3H).

(b) [1-(3,5-di-tert-butyl-4-hydroxy-benzyl)-azetidin-3-yl]-N-hydroxy-urea

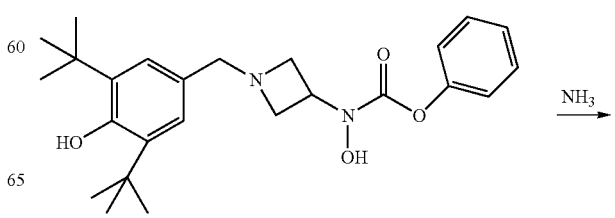

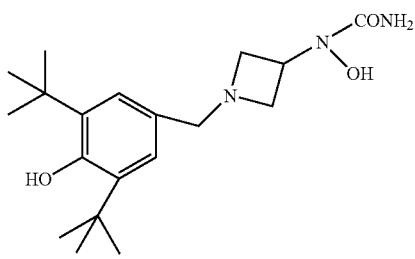

The product obtained according to step (a) (1,53 g, 3,6 mmols) was dissolved in 50 ml of Methanol and the solution was cooled to −78° C. under nitrogen atmosphere. A solution of 5.4 ml of $NH_3$ condensed in 12.7 ml of Methanol at −78° C. was added, the mixture was allowed to warm up to mom temperature and stirred at this temperature in a closed reactor, thereby controlling the progress of the reaction via Thin-layer-chromatography (TLC) after two hours. If any unreacted starting product is detected another portion of $NH_3$ may be added and the reaction kept stirring overnight. The solution was concentrated using a rotavapor and the crude material was purified via column chromatography (silica gel, eluent: chloroform/methanol 95:5 (volume/volume) to give 0,58 g of the desired product (47% of theoretical yield) having a melting point of 90–95° C.

IR (KBr, cm$^{-1}$): 3650, 3494, 3338, 2903, 1656, 1569, 1431, 1363, 1213. $^1$H-NMR (CDCl$_3$, δ): 1,4 (s, 18H), 3,5 (m, 4H), 3,6 (s, 2H), 4,8 (m, $_1$H), 5,2 (bs, 1H), 5,6 (bs, 2H), 7,0 (s, 2H).

Example 16

Synthesis of (2S,3R)-N-[1-(3,5-di-tert-butyl-4-hydroxy-benzoyl)-2-methyl-azetidin-3-yl]-2,2,2-trifluoro-acetamide a) 3,5-Di-tert-butyl-4-hydroxy-benzoyl chloride 3,5-Di-tert-butyl-4-hydroxy-benzoyl chloride was prepared according to step (a) of example 1.

b) N-[1-(3,5-di-tert-butyl-4-hydroxy-benzoyl)-(2S,3R)-2-methyl-azetidin-3-yl]-2,2,2-trifluoro-acetamide

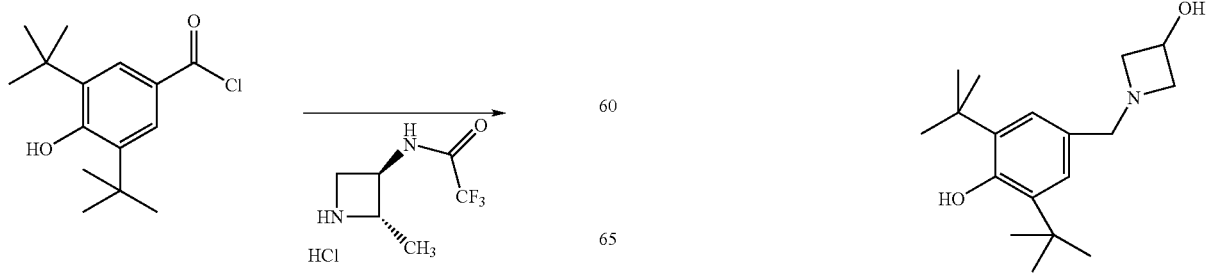

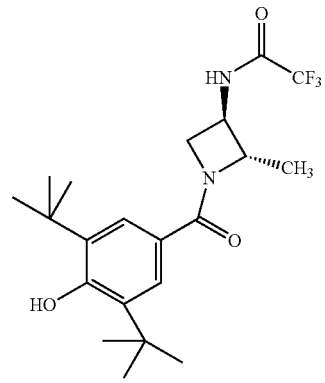

(2S,3R)-2,2,2-trifluoro-N-(2-methyl-azetidin-3-yl)-acetamide (1,04 g, 4,74 mmoles) hydrochloride was dissolved in dichloromethane (30 ml) and triethylamine (2,7 ml) was added, the mixture stirred for 10 minutes at room temperature, cooled to 0° C. and a solution of 3,5-di-tert-butyl-4-hydroxy-benzoyl chloride (1,16 g, 4,3 mmoles) in dichloromethane (20 ml) was added. The reaction mixture was stirred at room temperature overnight, then poured on ice, the phases were separated, the aqeous phase extracted with dichloromethane and the combined organic phases were dried over magnesium sulfate, filtered and evaporated to dryness to give 1,42 g (80% of theoretical yield) of N-[1-(3,5-di-tert-butyl-4-hydroxy-benzoyl)-(2S,3R)-2-methyl-azetidin-3-yl]-2,2,2-trifluoro-acetamide.

IR (KBr, cm$^{-1}$) 2967, 1722, 1618, 1560, 1420, 1225, 1187, 1160. $^1$H NMR (CDCl$_3$, δ): 1,4 (s, 18H), 1,5 (s, 3H), 4,3 (m, 2H), 4,7 (m, 2H), 5,5 (s, 1H), 7,3 (s, 2H), 9,0 (d, 1H)

Example 17

Synthesis of 1-(3,5-di-tert-butyl-4-hydroxy-benzyl)-azetidin-3-ol

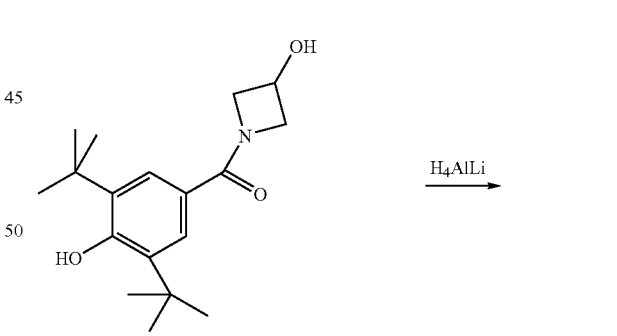

A suspension of lithium aluminium hydride (1,35 g, 36,7 mmoles) in anhydrous tetrahydrofuran (60 ml) was cooled to 0° C., and a solution of (3,5-di-tert-butyl-4-hydroxy-phenyl)-(3-hydroxy-azetidin-1-yl)-methanone (1,78 g, 6,12 mmoles) in anhydrous tetrahydrofuran (40 ml) was added. The cooling bath was removed, the mixture was stirred at room temperature overnight and then heated to reflux for 5 hours. The mixture was then cooled to 0° C. and the excess of the reducing agent was eliminated by the addition of a saturated solution of ammonium chloride. The mixture is filtered and the filtrate was evaporated to dryness by use of a rotavapor. The residue was dissolved in diethyl ether, the resulting solution washed with water, dried over sodium sulfate and evaporated to dryness with a rotavapor. The resulting crude solid was crystallized from chloroform/petrol ether to give 1,33 g (75% of theoretical yield) of the desired product having a melting point of 139–142° C.

IR (KBr, cm$^{-1}$): 3513, 3331, 3076, 2956, 1434, 1360, 1162, 788. $^1$H NMR (CDCl$_3$, δ): 1,4 (s, 18H), 2,7 (bs, 1H), 2,9 (dd, 2H), 3,5 (s, 2H), 3,6 (dd, 2H), 4,4 (m, 1H), 5,1 (s, 1H), 7,0 (s, 2H).

Example 19

Synthesis of 3-hydroxy-azetidine-1-carboxylic Acid 3,5-di-tert-butyl-phenyl ester (a) 3,5-Di-tert-butyl-phenyl chloroformiate

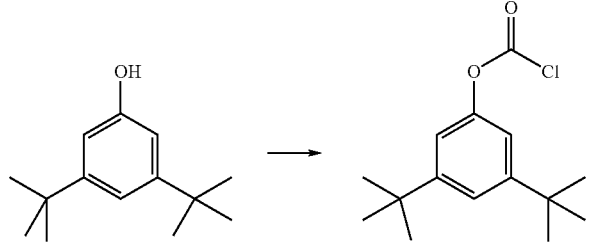

A solution of 3,5-di-tert-butyl-phenol (3,6 g, 17,4 mmoles) in 30 ml of tetrahydrofuran was cooled to 0° C. and a solution of trichloro methyl chloroformiate (2,9 ml, 22,56 mmoles) in 20 ml of tetrahydrofurane was added. The cooling bath was removed and the mixture was stirred at room temperature overnight. The solution so obtained was used in the following step.

(b) 3-Hydroxy-azetidine-1-carboxylic Acid 3,5-di-tert-butyl-phenyl ester

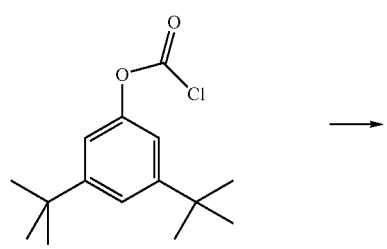

-continued

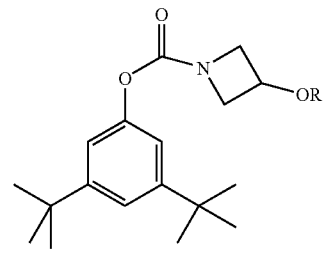

3-azetidinol hydrochloride (2.47 g, 22,62 mmoles) was suspended in tetrahydrofurane (30 ml), triethylamine (19 ml) was added and the mixture was heated to reflux for 30 minutes. The mixture was then cooled to room temperature and the solution of the chloroformiate according to step (a) was slowly added via a canule. The reaction mixture was heated to reflux overnight, cooled and filtered. The filtrate is evaporated to dryness in a rotavapor and the residue is purified via column chromatography (silica gel, eluent: ethyl acetate petrol ether 3:7 volume/volume). 0,83 g of 3-hydroxy-azetidine-1-carboxylic acid 3,5-di-tert-butyl-phenyl ester were obtained in form of a white solid having a melting point of 166–70° C.

IR (KBr, cm$^{-1}$) 3481, 2962, 1700, 1612, 1400.

$^1$H NMR(CDCl$_3$, δ): 1,3 (s, 18H), 2,7 (m, 1H), 4,0 (m, 2H), 4,3 (m, 2H), 4,6 (m, 1H), 6,9 (s, 2H), 7,3 (s, 1H).

The compounds of examples 2 and 11 were prepared according to the method described in example 1. The compounds of examples 4, 7, 9, 10, 12, 13, 17 and 18 were prepared according to the method described in example 3. The compound of example 14 was prepared analoguesly to the method described in J. M. Janusz et al., J. Med. Chem., 1998, 41(7), 1112–1123. The respective description is incorporated by reference and forms part of the disclosure.

The compounds of examples 1–4, 7, and 9–19 and their spectroscopic data is given in the following tables 1 and 2:

TABLE 1

| Z | Example | R$^4$ | R$^5$ | R$^6$ |
|---|---|---|---|---|
| ![3,5-di-tert-butyl-4-hydroxyphenyl] | 1 | H | OH | H |

TABLE 1-continued

| Z | Example | R⁴ | R⁵ | R⁶ |
|---|---|---|---|---|
| 3,5-di-tert-butylphenyl ketone | 2 | H | OH | H |
| 3,5-di-tert-butyl-4-hydroxyphenyl ketone | 3 | H | OH | CH₃ |
| 3,5-di-tert-butyl-4-hydroxyphenyl ketone | 4 | CH₃ | OH | H |
| 3,5-di-tert-butyl-4-hydroxyphenyl ketone | 7 | H | Br | H |
| 3,5-di-tert-butyl-4-methoxyphenyl ketone | 9 | H | OH | H |
| 3,5-diisopropyl-4-hydroxyphenyl ketone | 10 | H | OH | H |
| 3,5-di-tert-butylphenyl ketone | 11 | H | O(CH₂)₄ONO₂ | H |
| 3,5-di-tert-butyl-4-hydroxyphenyl ketone | 12 | Ph | OH | H |
| 3,5-di-tert-butyl-4-hydroxyphenyl ketone | 13 | H | Ph | OH |
| benzofuran derivative ketone | 14 | H | OH | H |

TABLE 1-continued

| Z | Example | R⁴ | R⁵ | R⁶ |
|---|---------|----|----|----|
| 3,5-di-tert-butyl-4-hydroxybenzyl | 15 | H | N(OH)CONH₂ | H |
| 3,5-di-tert-butyl-4-hydroxybenzyl | 16 | CH₃ | NHCOCF₃ | H |
| 3,5-di-tert-butyl-4-hydroxybenzoyl | | | | |

TABLE 1-continued

| Z | Example | R⁴ | R⁵ | R⁶ |
|---|---------|----|----|----|
| 3,5-di-tert-butyl-4-hydroxybenzyl | 17 | H | OH | H |
| 3,5-di-tert-butyl-4-hydroxyphenacyl | 18 | H | OH | H |
| 3,5-di-tert-butylphenyl acetate | 19 | H | OH | H |

TABLE 2

| Example | Melting point °C. | IR (KBr, cm⁻¹) | ¹H NMR (CDCl₃, δ) |
|---------|-------------------|----------------|---------------------|
| 1 | 185–9 | 3506, 3262, 2956, 1611, 1572, 1449, 1421, 1406, 1113 | 1.43(s, 18H), 2.8(bs, 1H), 4.0–4.2(m, 2H), 4.45(m, 2H), 4.7(m, 1H), 5.5(s, 1H), 7.5(s, 2H) |
| 2 | 146–9 | 3444, 3344, 3287, 2957, 1613, 1587, 1456, 1125 | 1.3(s, 18H), 3.5(d, 1H), 4.0–4.2(m, 2H), 4.4(dd, 2H), 4.6(m, 1H), 7.4(s, 2H), 7.5(s, 1H). |
| 3 | 148–53 | 3497, 3274, 2963, 1612, 1598, 1415, 1235, 1120 | 1.4(s, 18H), 1.5(s, 3H), 3.9(s, 1H), 4.1(m, 3H), 4.3(m, 1H), 5.5(s, 1H), 7.5(s, 2H). |
| 4 | 162–6 | 3469, 3250, 2960, 1608, 1571, 14011239, 1090 | 1.4(s, 21H), 3.3(bs, 1H), 3.9(m, 1H), 4.1(m, 1H), 4.4(m, 2H), 5.5(s, 1H), 7.5(s, 2H). |
| 7 | 160–3 | 3506, 2953, 1632, 1600, 1383, 1131, 1110 | 1.4(s, 18H), 4.4–4.8(m, 5H), 7.5(s, 2H) |
| 9 | 115–120 | 3296, 2963, 1602, 1555, 1474, 1449, 1410, 1396 | 1.4(s, 18H), 3.7(s, 3H), 3.9–4.2(m, 3H), 4.4(m, 2H), 4.7(m, 1H), 7.5(s, 2H) |

TABLE 2-continued

| Example | Melting point ° C. | IR (KBr, cm$^{-1}$) | $^1$H NMR (CDCl$_3$, δ) |
|---|---|---|---|
| 10 | 156–60 | 3330, 1615, 1605, 1565, 1463, 1433, 1412, 1202 | 1.3(s, 12H), 3.4(m, 2H), 4.1–4.3(m, 3H), 4.4–4.6(m+s, 3H), 4.7(m, 1H), 7.4(s, 2H) |
| 11 | oil | 2962, 1637, 1594, 1459, | 1.3(s, 18H), 1.7(m, 2H), 1.8(m, 2H), 3.4(m, 2H), 4.0–4.15(m, 2H), 4.3–4.4 (m, 3H), 4.5(t, J=6.3Hz, 2H), 7.4(s, 2H), 7.5(s, 1H) |
| 12 | 178–81 | 3400, 3310, 2956, 1607, 1570, 1395, | 1.3(s, 18H), 3.7(d, 1H), 4.1(dd, 1H), 4.3(m, 1H), 4.6(m, 1H), 5.3(bs, 1H), 5.45(bs, 1H), 7.3–7.4(m, 7H) |
| 13 | 163–5 | 3530–3300, 2956, 1606, 1452, 1116 | 1.43(s, 18H), 3.3(bs, 1H), 4.4–4.6(m, 4H), 5.5(s, 1H), 7.4(m, 3H), 7.5(m, 4H) |
| 14 | 144–8 | 3265, 2955, 1603, 1582, 1450, 1410, 1129, 995, 956 | 1.31(s, 6H), 1.34(s, 9H), 3.2(bs, 1H), 4.0–4.3(m+s, 4H), 4.45(m, 2H), 4.7 (m, 1H), 7.3(s, 1H), 7.35(s, 1H). |
| 15 | 90–5 | 3650, 3494, 3338, 2903, 1656, 1569, 1431, 1363, 1213 | 1.4(s, 18H), 3.5(m, 4H), 3.6(s, 2H), 4.8(m, 1H), 5.2(bs, 1H), 5.6(bs, 2H), 7.0(s, 2H) |
| 16 | amorph | 2967, 1722, 1618, 1560, 1420, 1225, 1187, 1160 | 1.4(s, 18H), 1.5(s, 3H), 4.3(m, 2H), 4.7(m, 2H), 5.5(s, 1H), 7.3(s, 2H), 9.0(d, 1H) |
| 17 | 139–42 | 3513, 3331, 3076, 2956, 1434, 1360, 1162, 788 | 1.4(s, 18H), 2.7(bs, 1H), 2.9(dd, 2H), 3.5(s, 2H), 3.6(dd, 2H), 4.4(m, 1H), 5.1(s, 1H), 7.0(s, 2H) |
| 18 | 154–6 | 2295, 2955, 1637, 1435, 1100 | 1.43(s, 18H), 3.0(d, 1H), 3.36(s, 2H), 3.8(dd, 1H), 4.0(dd, 1H), 4.2(t, 1H), 4.3(t, 1H), 4.6(m, 1H), 7.0(s, 2H) |
| 19 | 166–70 | 3481, 2962, 1700, 1612, 1400 | 1.3(s, 18H), 2.7(m, 1H), 4.0(m, 2H), 4.3(m, 2H), 4.6(m, 1H), 6.9(s, 2H), 7.3(s, 1H) |

Pharmacological Data:

I. Cox-1/Cox-2 Enzyme Assay:

The Cox-1/Cox-2 enzyme assay for the inventive azetidine compounds was carried out as described above. The values for enzyme inhibition of some inventive compounds are given in the following table I.

TABLE I

| Compound according to | % inhibition 5 × 10$^{-5}$ M | | IC$_{50}$ µM | |
|---|---|---|---|---|
| Example | COX-1 | COX-2 | COX-1 | COX-2 |
| 1 | — | — | 37.7 | 1.51 |
| 2 | 9 | 78 | — | 1.8 |
| 3 | — | — | 349 | 3.51 |
| 4 | — | — | 246 | 3.75 |
| 7 | 35 | — | — | 0.2 |
| 14 | — | — | 48.3 | 0.6 |
| 18 | 4 | 1 | — | — |

II. Determination of Cox-1- and Cox-2-activity in Human Whole Blood

The Cox-1- and Cox-2-activity in human whole blood is determined as described above. The values of some inventive compounds are given in the following table II.

TABLE II

| Compound according to Example | hWB inhibition COX-1 IC$_{50}$ (µM) | hWB inhibition COX-2 IC$_{50}$ (µM) |
|---|---|---|
| 1 | 0.1 | 0.2 |
| 2 | 0.5 | 0.8 |
| 3 | 0.1 | 0.1 |
| 4 | 0.5 | 0.5 |
| 14 | 0.05 | 0.1 |

III: Analgesia Test in Rats

The test of the inventive compounds for analgesic activity was carried out as described above. The values for some of the inventive compounds is given in the following table III.

TABLE III

| Compound according to Example | ED$_{50}$ (mg/Kg) |
|---|---|
| 1 | 0.4 |
| 2 | 1.65 |
| 3 | 0.14 |
| 4 | 0.7 |
| 14 | 3 |

IV. Test for Activity Against Edema in Rats

The test for activity against edema was carried out as described above. The values of some of the inventive compounds are given in the following table IV:

TABLE IV

| Compound according to Example | ED$_{50}$ (mg/kg) |
|---|---|
| 1 | 3 |
| 2 | 28 |
| 3 | 58 |
| 4 | 31 |
| 17 | 62 |

V: Test for Antiarthritic Activity in Rats

The test for antiarthritic activity was carried out as described above. The values of some of the inventive compounds are given in the following table V.

TABLE V

| Compound according to Example | ED$_{50}$ (mg/kg) |
|---|---|
| 1 | 0.5 |
| 3 | 0.34 |

VI: PGE2 Production in Rat Inflammatory Exudate and Gastric Mucosa

The PGE2 production rat inflammatory exudate and gastric mucosa was carried out as described above. The values for some of the inventive compounds are given in the following table VI.

TABLE VI

| Example | PGE$_2$ gastric mucose ED$_{50}$ (mg/kg) | PGE$_2$ Inflam. exudade ED$_{50}$ (mg/kg) |
|---|---|---|
| 1 | 0.16 | 0.28 |
| 2 | 3.7 | 5.9 |
| 3 | 7.3 | 0.5 |
| 4 | 1.0 | 5.8 |
| 14 | 2.7 | 1.8 |

The invention claimed is:

1. An Azetidine compound of formula I,

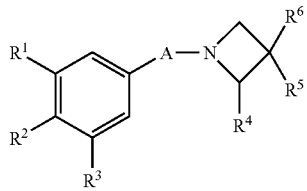

wherein
A represents a —C═O-moiety,
R$^1$, R$^3$, identical or different, represent a hydrogen atom or a linear or branched, saturated or unsaturated C$_{1-4}$-aliphatic group,
R$^2$ represents a hydroxyl group or a C$_{1-3}$-alkoxy group, or R$^1$ and R$^2$ or R$^2$ and R$^3$ together form an —O—CH$_2$—CH$_2$-moiety, which is optionally substituted with one or more methyl groups
R$^4$ represents a hydrogen atom, an optionally at least mono-substituted aryl group, or a linear or branched, saturated or unsaturated aliphatic group, which may be substituted by one or more substituents independently selected from the group consisting of hydroxy, fluorine, chlorine, bromine, branched or unbranched C$_{1-4}$-alkoxy, branched or unbranched C$_{1-4}$-perfluoroalkoxy and branched or unbranched C$_{1-4}$-perfluoroalkyl,
R$^5$ represents a hydrogen atom, a halogen atom, a hydroxyl group, a linear or branched, saturated or unsaturated, optionally at least mono-substituted aliphatic group,
R$^6$ represents a hydrogen atom, a halogen atom, a hydroxyl group, a linear or branched, saturated or unsaturated, optionally at least mono-substituted aliphatic group,
with the provisos
that if R$^2$ is alkoxy, at least one of R$^1$, R$^3$, R$^4$, R$^5$ and R$^6$ does not represent a hydrogen atom,
that if R$^4$ represents a hydrogen atom and one of the residues R$^5$ and R$^6$ represents a hydrogen atom, then the other one of these residues R$^5$ and R$^6$ does not represent a methyl group, which is substituted by an —NH$_2$-moiety or an azaheterocycle, and
optionally in form of one of the stereoisomers, a racemate or in form of a mixture of at least two of the stereoisomers, in any mixing ratio, or a corresponding salt thereof, or a corresponding solvate thereof.

2. A compound according to claim 1, characterized in that R$^1$ and R$^3$, identical or different, represent a hydrogen atom or a linear or branched C$_{1-4}$-alkyl group.

3. A compound according to claim 1, characterized in that R$^1$ and R$^3$ are identical and represent a C$_{1-4}$-alkyl group.

4. A compound according to claim 1, characterized in that R$^2$ represents a hydroxyl group or a methoxy group.

5. A compound according to claim 1, characterized in that R$^4$ represents a hydrogen atom, an optionally at least mono-substituted phenyl group, or a linear or branched, saturated or unsaturated CF$_{1-6}$ aliphatic group, whereby said aliphatic group may be substituted by one or more substituents independently selected from the group consisting of hydroxy, fluorine, chlorine, bromine, branched or unbranched C$_{1-4}$-alkoxy, branched or unbranched C$_{1-4}$-perfluoroalkoxy and branched or unbranched C$_{1-4}$-perfluoroalkyl, preferably a hydrogen atom, a methyl group or an unsubstituted phenyl group.

6. A compound according to claim 5, characterized in that R$^5$ represents a hydrogen atom, a halogen atom, a hydroxyl group, a linear or branched, saturated or unsaturated, optionally at least mono-substituted C$_{1-6}$ aliphatic group.

7. A compound according to claim 1, characterized in that R$^6$ represents a hydrogen atom, a halogen atom, a hydroxyl group, a linear or branched, saturated or unsaturated, optionally at least mono-substituted C$_{1-6}$ aliphatic group.

8. A compound according to claim 1 of formula I,

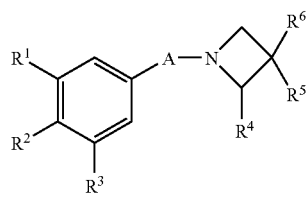

wherein
A represents a —C═O-moiety,
R$^1$, R$^3$ both identically represent an iso-propyl group or a tert-butyl group,
R$^2$ represents a hydroxyl group or a methoxy group, or $R^1$ and $R^2$ or $R^2$ and $R^3$ together form an —O—CH$_2$—C(CH$_3$)$_2$-chain, whereby the oxygen atom of said chain is bonded to the 4-position of the phenyl ring, $R^4$ represents a hydrogen atom, a methyl group or an unsubstituted phenyl group, $R^5$ represents a bromine atom, or a hydroxyl group, $R^6$ represent a hydrogen atom, a methyl group or a hydroxyl group, optionally in form of one of the stereoisomers, a racemate or in form of a mixture of at least two of the stereoisomers, in any mixing ratio, or a corresponding salt thereof, or a corresponding solvate thereof.

9. A compound according to claim 1 selected from the group consisting of

[1] (3,5-di-tert-butyl-4-hydroxy-phenyl)-(3-hydroxy-azetidin-1-yl)-methanone;

[3] (3,5-di-tert-butyl-4-hydroxy-phenyl)-(3-hydroxy-3-methyl-azetidin-1-yl)-methanone;

[4] (3,5-di-tert-butyl-4-hydroxy-phenyl)-(3-hydroxy-2-methyl-azetidin-1-yl)-methanone;

[7] (3-Bromo-azetidin-1-yl)-(3,S-di-tert-butyl-4-hydroxy-phenyl)-methanone;

[9] (3,5-di-tert-butyl-4-methoxy-phenyl)-(3-hydroxy-azetidin-1-yl)-methanone;

[10] (3-hydroxy-azetidin-1-yl)-(4-hydroxy-3,S-diisopropyl-phenyl)-methanone;

[12] (3,5-di-tert-butyl-4-hydroxy-phenyl)-(3-hydroxy-2-phenyl-azetidin-1-yl)-methanone; and

[14] (7-tert-butyl-3,3-dimethyl-2,3-dihydro-benzofuran-5-yl)-(3-hydroxy-azetidin-1-yl)-methanone;

optionally in form of a corresponding salt or a corresponding solvate.

10. A process for the preparation of an azetidine compound of formula I according to claim 1, characterized in that at least one compound of formula II,

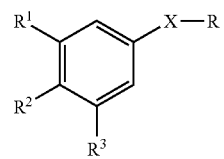

II wherein $R^1$–$R^3$ have the meaning according to claim 1, X represents a bond and R represents a carboxy group or an activated carbonyl group, is reacted with at least one compound of formula III,

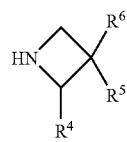

III optionally in the form of a corresponding salt, wherein $R^4$–$R^6$ have the meaning according to claim 1, to yield a compound of formula I according to claim 1, wherein A represents a —(C=O)-moiety which is optionally purified and/or optionally isolated.

11. A medicament comprising at least one azetidine compound according to claim 1 and one or more pharmaceutically acceptable excipients.

12. A method for the treatment of pain comprising administering to a patient in need thereof a pain inhibiting amount of the medicament according to claim 11.

13. A method for the treatment of inflammation comprising administering to a patient in need thereof an inflammation inhibiting amount of the medicament according to claim 11.

14. A method for the treatment of inflammation according to claim 13 where the inflammation is the result of a disorder selected from the group consisting of arthritis, rheumatoid arthritis, spondyloarthropathies, gouty arthritis, osteoarthritis, systemic lupus erythematosus, juvenile arthritis, rheumatic fever, lower back pain, neck pain, dysmenorrhea, headache, toothache, sprains, strains, myositis, neuralgia, synovitis, gout, ankylosing spondylitis, bursitis, edema, migraine headaches, periarteritis nodosa, thyroiditis, aplastic anemia, scleroderma, myasthenia gravis, sarcoidosis, nephrotic syndrome, Behcet's syndrome, polymyositis, gingivitis, hypersensivity, conjunctivitis, and myocardia ischemia.

15. A compound according to claim 1 where the stereoisomers are enantiomers or diastereomers.

16. A compound of claim 3 where the $C_{1-4}$-alkyl group, is a $C_{3-4}$ alkyl group.

17. A compound of claim 3 where a $C_{1-4}$-alkyl group, is an iso-propyl group or a tert.-Butyl group.

18. A compound of claim 1 where $R^6$ represents a hydrogen atom, a hydroxyl group or a methyl group.

19. A compound according to claim 1, characterized in that $R^7$, $R^8$, $R^9$, $R^{10}$, independent from one another, represent a linear or branched $C_{1-6}$ alkyl group.

20. A medicament comprising at least one azetidine compound according to claim 2 and one or more pharmaceutically acceptable excipients.

21. A medicament comprising at least one azetidine compound according to claim 3 and one or more pharmaceutically acceptable excipients.

22. A medicament comprising at least one azetidine compound according to claim 4 and one or more pharmaceutically acceptable excipients.

23. A medicament comprising at least one azetidine compound according to claim 5 and one or more pharmaceutically acceptable excipients.

24. A medicament comprising at least one azetidine compound according to claim 6 and one or more pharmaceutically acceptable excipients.

25. A medicament comprising at least one azetidine compound according to claim 7 and one or more pharmaceutically acceptable excipients.

26. A medicament comprising one or more pharmacologically acceptable excipients and at least one azetidine compound of formula I,

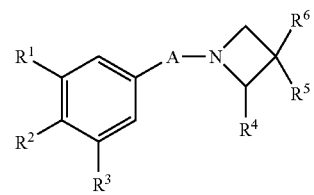

wherein

A represents a —C=O-moiety, $R^1$, $R^3$, identical or different, represent a hydrogen atom or a linear or branched, saturated or unsaturated $C_{1-4}$-aliphatic group, $R^2$ represents a hydroxyl group or a $C_{1-3}$-alkoxy group, or $R^1$ and $R^2$ or $R^2$ and $R^3$ together form an —O—CH$_2$—CH$_2$-moiety, which is optionally substituted with one or more methyl groups, $R^4$ represents a hydrogen atom, an optionally at least mono-substituted aryl group, or a linear or branched, saturated or unsaturated aliphatic group, which may be substituted by one or more substituents independently selected from the group consisting of hydroxy, fluorine, chlorine, bromine, branched or unbranched $C_{1-4}$-alkoxy, branched or unbranched $C_{1-4}$-perfluoroalkoxy and branched or unbranched $C_{1-4}$-perfluoroalkyl, $R^5$ represents a hydrogen atom, a halogen atom, a hydroxyl group, a linear or branched, saturated or unsaturated, optionally at least mono-substituted aliphatic group, $R^6$ represents a hydrogen atom, a halogen atom, a hydroxyl group, a linear or branched, saturated or unsaturated, optionally at least mono-substituted aliphatic group with the provisos that if $R^2$ is alkoxy, at least one of $R^1$, $R^3$, $R^4$, $R^5$ and $R^6$ does not represent a hydrogen atom, that if $R^4$ represents a hydrogen atom and one of the residues $R^5$ and $R^6$ represents a hydrogen atom, then the other one of these residues $R^5$ and $R^6$ does not represent a methyl group, which is substituted by an —NH$_2$-moiety or an azaheterocycle, and optionally in form of one of the stereoisomers, a racemate or in form of a mixture of at least two of the stereoisomers, in any mixing ratio, or a corresponding salt thereof, or a corresponding solvate thereof.

* * * * *